(12) United States Patent
Nicolau

(10) Patent No.: US 7,067,133 B2
(45) Date of Patent: Jun. 27, 2006

(54) METHODS AND COMPOSITIONS FOR DISEASES ASSOCIATED WITH AMYLOIDOSIS

(75) Inventor: Yves Claude Nicolau, Newton, MA (US)

(73) Assignees: Aventis Pharma S.A., Anthony (FR); Université Louis Pasteur, Strasbourg (FR)

( * ) Notice: Subject to any disclaimer, the term of this patent is extended or adjusted under 35 U.S.C. 154(b) by 0 days.

(21) Appl. No.: 09/948,049

(22) Filed: Sep. 6, 2001

(65) Prior Publication Data

US 2002/0156036 A1 Oct. 24, 2002

Related U.S. Application Data

(60) Provisional application No. 60/230,391, filed on Sep. 6, 2000, provisional application No. 60/255,033, filed on Dec. 12, 2000.

(51) Int. Cl.
*A61K 39/00* (2006.01)
*A61K 39/385* (2006.01)
*A01N 25/26* (2006.01)
*A01K 38/00* (2006.01)
*C07K 16/00* (2006.01)

(52) U.S. Cl. ............... 424/185.1; 424/450; 424/193.1; 424/194.1; 424/420; 530/326; 530/323; 530/300; 514/2

(58) Field of Classification Search ................. 424/450, 424/283.1, 460, 420, 185.1, 193.1; 530/300, 530/323, 326; 514/2
See application file for complete search history.

(56) References Cited

U.S. PATENT DOCUMENTS 6,743,427 B1 6/2004 Schenk
6,787,637 B1 9/2004 Schenk

FOREIGN PATENT DOCUMENTS

WO WO 99/27944 * 6/1999

OTHER PUBLICATIONS

Walter et al., 1997, Biochem and Biophys Research Comm, 233, pp. 760-764.*
Glenner, M.D., George G., et al., "Alzheimer's Disease: Initial Report of the Purification and Characterization of a Novel Cerebrovascular Amyloid Protein", Biochemical and Biophysical Research Communications, vol. 120, No. 3, pp. 885-890 (1984).
Potter, Huntington, et al., "The Potential of BACE Inhibitors for Alzheimer's Therapy", Nature Biotechnology, vol. 18, pp. 125-126 (2000).
Schenk, Dale, et al., "Immunization with Amyloid-β Attenuate Alzheimer-Disease-Like Pathology in the PDAPP Mouse", Nature, vol. 400, pp. 173-177 (1999).
Solomon, Beka, et al., "Disaggregation of Alzheimer β-Amyloid by Site-Directed MAb", Proc. Natl. Acad. Sci. USA, vol. 94, pp. 4109-4112 (1997).
Tamaoka, Akira, et al., "Identification of a Stable Fragment of the Alzheimer Amyloid Precursor Containing the β-protein in Brain Microvessels", Proc. Natl. Acad. Sci. USA, vol. 89, pp. 1345-1349 (1992).
Tosi, Pierre-François, et al., "Immune Response Against the Murine MDRI Protein Induced by Vaccination With Synthetic Lipopeptides in Liposomes", Biochemical and Biophysical Research Communications, vol. 212, No. 2, pp. 494-500 (1995).

* cited by examiner

*Primary Examiner*—Olga N. Chernyshev
(74) *Attorney, Agent, or Firm*—Kilpatrick Stockton LLP

(57) ABSTRACT

The present invention generally relates to the detection, treatment or prevention of disease states. Specifically, the present invention relates to the detection, treatment or prevention of amyloidosis or amyloid-associated diseases. The present invention further comprises methods and compositions comprising therapeutic vaccines, antisera and molecular constructs, comprising expression vectors and fusion proteins encoded therein.

12 Claims, 11 Drawing Sheets

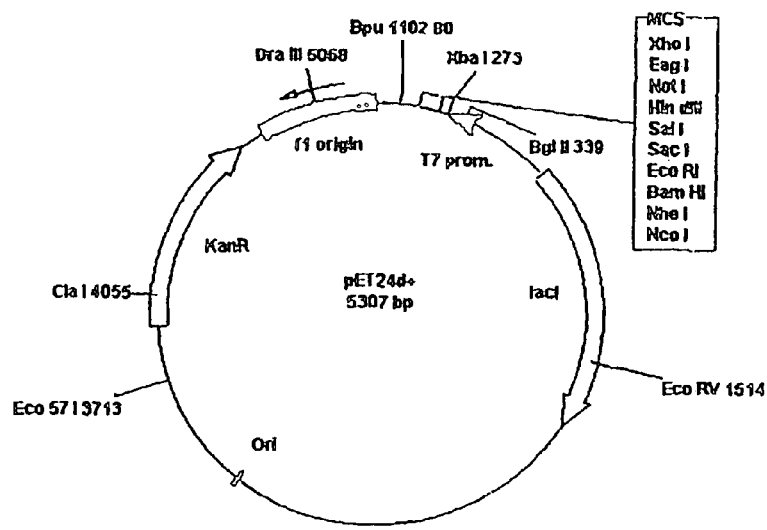

FIG. 2A

SEQ ID NO: 3

<u>Bgl II</u>      <u>T7 promoter</u>                                          <u>Xba I</u>
   <u>rba</u>
AGATCTGATCCCGCGAAATTAATACGACTCACTATAGGGGAATTGTGAGCGGATAACAATTCCCCTCTAGAAAT
AAT

TTTGTTTACTTTAAGAAGGAGA

<u>NcoI</u>  <u>NheI</u>                    <u>BamHI</u> <u>EcoRI</u> <u>SacI</u>   <u>SalI</u>   <u>HindIII</u>
<u>NotI</u>
<u>XhoI</u>

TATACC<u>ATGGCTAGC</u>ATGACTGGTGGACAGCAAATGGGTCGGATCCGAATTCGAGCTCCGTCGACAAGCTTGCGGC
C
GCACTCGAG<u>CACCACCACCACCACCACCAC</u>TGA
         T7 -    Tag

His - Tag

FIG. 2B pETVL112 = pET36 + VL

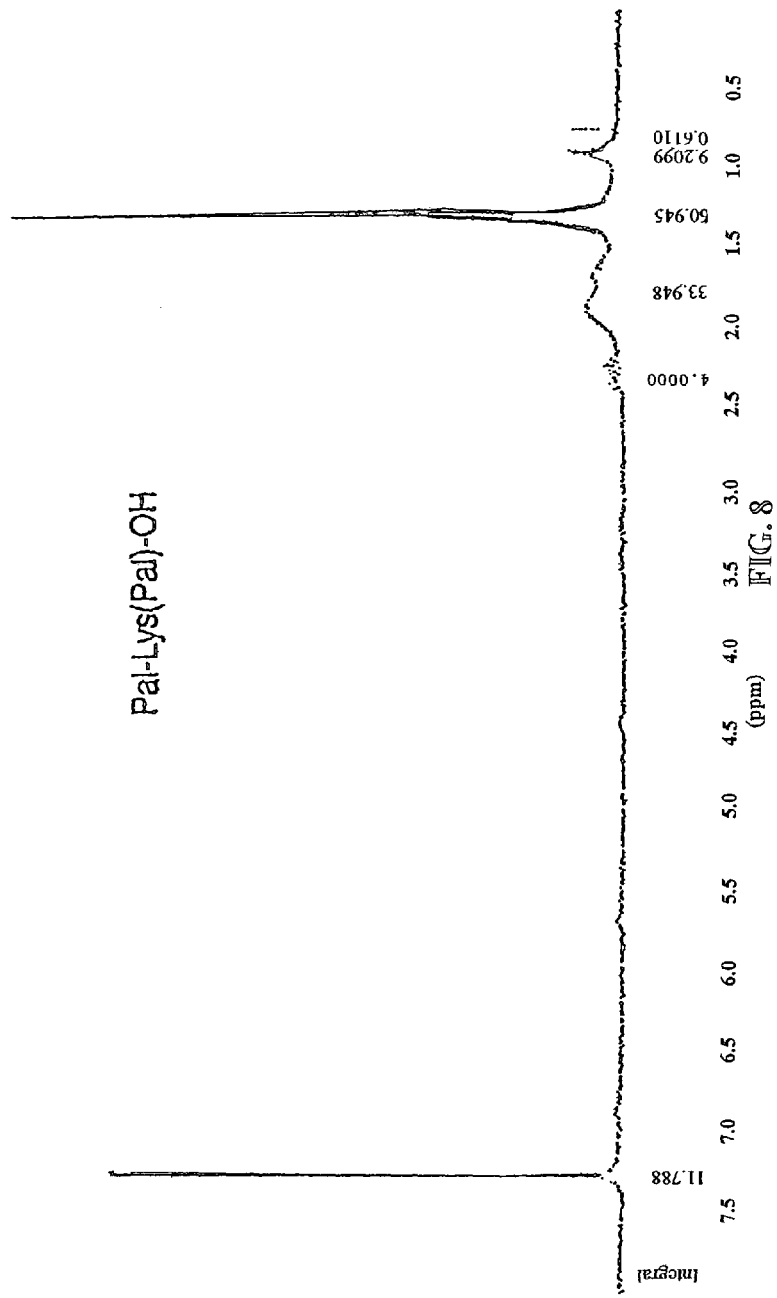

SEQUENCE LISTING

<160> NUMBER OF SEQ ID NOS: 3

<210> SEQ ID NO 1
<211> LENGTH: 333
<212> TYPE: DNA
<213> ORGANISM: Murinae gen. sp.
<220> FEATURE:
<221> NAME/KEY: CDS
<222> LOCATION: (1)..(333)
<223> OTHER INFORMATION:

<400> SEQUENCE: 1

| atg | gat | gtg | ctc | atg | acc | cag | acg | ccg | ctc | agc | ctg | ccg | gtg | agc | ctg | 48 |
| Met | Asp | Val | Leu | Met | Thr | Gln | Thr | Pro | Leu | Ser | Leu | Pro | Val | Ser | Leu | |
| 1 | | | | 5 | | | | | 10 | | | | | 15 | | |

| ggc | gat | cag | gcg | agt | att | tct | tgc | cgt | tcc | agc | cag | aac | att | atc | cat | 96 |
| Gly | Asp | Gln | Ala | Ser | Ile | Ser | Cys | Arg | Ser | Ser | Gln | Asn | Ile | Ile | His | |
| | | | 20 | | | | | 25 | | | | | 30 | | | |

| agc | aac | ggc | aat | acc | tat | ctg | gaa | tgg | tac | ctg | cag | aaa | ccc | ggc | cag | 144 |
| Ser | Asn | Gly | Asn | Thr | Tyr | Leu | Glu | Trp | Tyr | Leu | Gln | Lys | Pro | Gly | Gln | |
| | | 35 | | | | | 40 | | | | | 45 | | | | |

| agc | ccg | aaa | ctg | ctg | att | tat | aaa | gtg | agc | aac | cgc | ttt | agc | ggt | gtg | 192 |
| Ser | Pro | Lys | Leu | Leu | Ile | Tyr | Lys | Val | Ser | Asn | Arg | Phe | Ser | Gly | Val | |
| | 50 | | | | | 55 | | | | | 60 | | | | | |

| ccg | gat | cgt | ttt | agc | ggc | agt | ggt | agc | ggc | acc | gat | ttt | acc | ctg | aaa | 240 |
| Pro | Asp | Arg | Phe | Ser | Gly | Ser | Gly | Ser | Gly | Thr | Asp | Phe | Thr | Leu | Lys | |
| 65 | | | | | 70 | | | | | 75 | | | | | 80 | |

| att | aaa | aag | gtg | gaa | gcg | gaa | gat | ctg | ggc | att | tat | tat | tgc | ttt | caa | 288 |
| Ile | Lys | Lys | Val | Glu | Ala | Glu | Asp | Leu | Gly | Ile | Tyr | Tyr | Cys | Phe | Gln | |
| | | | | 85 | | | | | 90 | | | | | 95 | | |

| ggt | agc | cat | gtg | ccg | ctg | acc | ttt | ggc | gcg | ggc | acc | aaa | ctc | gag | | 333 |
| Gly | Ser | His | Val | Pro | Leu | Thr | Phe | Gly | Ala | Gly | Thr | Lys | Leu | Glu | | |
| | | | 100 | | | | | 105 | | | | | 110 | | | |

<210> SEQ ID NO 2
<211> LENGTH: 111
<212> TYPE: PRT
<213> ORGANISM: Murinae gen. sp.

<400> SEQUENCE: 2

Met Asp Val Leu Met Thr Gln Thr Pro Leu Ser Leu Pro Val Ser Leu
1               5                   10                  15

Gly Asp Gln Ala Ser Ile Ser Cys Arg Ser Ser Gln Asn Ile Ile His
            20                  25                  30

Ser Asn Gly Asn Thr Tyr Leu Glu Trp Tyr Leu Gln Lys Pro Gly Gln
        35                  40                  45

Ser Pro Lys Leu Leu Ile Tyr Lys Val Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Lys Lys Val Glu Ala Glu Asp Leu Gly Ile Tyr Tyr Cys Phe Gln
                85                  90                  95

Gly Ser His Val Pro Leu Thr Phe Gly Ala Gly Thr Lys Leu Glu
            100                 105                 110

<210> SEQ ID NO 3
<211> LENGTH: 209
<212> TYPE: DNA
<213> ORGANISM: Artificial Sequence -continued

```
<220> FEATURE:
<223> OTHER INFORMATION: Synthetic plasmid

<400> SEQUENCE: 3
agatctgatc ccgcgaaatt aatacgactc actatagggg aattgtgagc ggataacaat      60
tcccctctag aaataatttt gtttacttta agaaggagat ataccatggc tagcatgact     120
ggtggacagc aaatgggtcg gatccgaatt cgagctccgt cgacaagctt gcggccgcac     180
tcgagcacca ccaccaccac caccactga                                       209
```

METHODS AND COMPOSITIONS FOR DISEASES ASSOCIATED WITH AMYLOIDOSIS

RELATED APPLICATIONS

This application claims priority to U.S. Provisional Application No. 60/230,391 filed on Sep. 6, 2000 and to U.S. Provisional Application No. 60/255,033 filed on Dec. 12, 2000.

FIELD OF THE INVENTION

The present invention generally relates to the detection, treatment or prevention of disease states. Specifically, the present invention relates to the detection, treatment or prevention of amyloidosis or amyloid-associated diseases.

BACKGROUND OF THE INVENTION

Amyloidosis includes a variety of diseases characterized by an accumulation of amyloid material in the organs or tissues of the body. This accumulation can impair vital functions. Diseases associated with amyloidosis include Alzheimer's disease (AD), Down's Syndrome, progressive supranuclear palsy, multiple sclerosis, and Adult Onset Diabetes. Localized amyloidosis is associated with cognitive decline (senile cerebral amyloidosis; Alzheimer's), heart disease (senile cardiac amyloidosis), endocrine tumors (thyroid cancer), and Adult Onset Diabetes, diseases which are found in millions of Americans.

A number of impairments specific to amyloid deposits in the brain are linked with the deposition of the peptide, A$\beta$ peptide (amyloid-$\beta$ peptide). Neurological diseases associated with A$\beta$ peptide deposition include Alzheimer's, Lewy body dementia, Down's Syndrome, hereditary cerebral hemorrhage with amyloidosis (Dutch type), and the Guamanian Parkinsonism-Dementia. A$\beta$ peptide plaques also occur in persons who have experienced head trauma and critical coronary disease.

The most common disease related to cognitive decline or dementia is Alzheimer's Disease (AD). This condition is characterized by neuronal loss, neurofibrillary tangles, and neuritic plaques comprised of A$\beta$ peptide. Due to the nature of cerebral amyloidosis, diagnosis of Alzheimer's before death is difficult and the development of therapies or other treatments for Alzheimer's have been elusive. Many proposed therapies are unable to cross the blood-brain barrier in amounts necessary for effective treatment.

It is currently believed that amyloid plaques in the brain are predominantly composed of A$\beta$ peptide, a 4 kD protein, 39–43 amino acids long. A$\beta$ peptide is expressed by a gene located on chromosome 21 and is derived by proteolytic cleavage from the interior of a much larger (770 residue) cell protein, amyloid precursor protein (APP). After excision, A$\beta$ peptide is polymerized into amyloid filaments, which in turn aggregate into amyloid plaque deposits. In the brain, these filaments and aggregates are toxic to neurons and are thought to relate to the causative symptoms associated with AD.

The inability to examine amyloid deposition of AD in patients before death impedes the ability of researchers to study AD and develop effective therapies targeted at preventing or reversing amyloid plaque formation on the brain. Damage to CNS neurons due to AD begins years before clinical symptoms are evident. Prevention of amyloidosis in the brain would prevent the development of AD. A similar approach to preventing or treating amylin plaque formation in Adult Onset Diabetes patients would also be beneficial.

Other investigations have identified a set of mutations that cause familial Alzheimer's disease (FAD), in an autosomal dominant manner. All known FAD mutations increase either the absolute or relative production of the most pathogenic A$\beta$ peptide with 42 amino acids. These mutations arise either in the APP gene itself, affecting the target sites in the APP where proteolytic cleavage occurs, or in one of two presenilin genes, the protein products which directly or, more probably, indirectly affect APP processing. The early step of AD excision is followed by the polymerisation of the peptide to amyloid filaments, which in turn aggregate into the visible amyloid plaque deposits that characterize the brains of individuals with AD. These filaments, or possibly intermediate protofilaments, are toxic to neurons and are thought to lead to neurofibrillary tangles, synapse loss, and neurodegeneration that underlie the decline of cognitive functions in Alzheimer's patients.

In addition to the production of the A$\beta$ peptide (amyloid-$\beta$ peptide), other important steps are involved in the pathogenic pathway leading to AD. Genetic and biochemical studies both assign a key role to a set of auxiliary proteins that function as "pathological chaperones". One such protein is the anti-protease, anti-chyrmotrypsin, and another is the lipid transport protein, apolipoprotein F, particularly its E4 allelic form. Both of these proteins promote the formation and maturation of Alzheimer's plaques with their core of A$\beta$ filaments. Specifically, the pathological chaperones can be demonstrated in vitro to accelerate the polymerisation of A$\beta$ into neurotoxic amyloid filaments, and experiments with transgenic mice support their role in promoting amyloid formation in vivo. Both proteins are minor components of the amyloid deposits, and are evidently produced as part of an inflammation reaction that arises in response to the initial diffuse deposition of A$\beta$ peptide.

What is needed are methods and compositions for diagnosis and treatment of amyloid-associated diseases.

SUMMARY OF THE INVENTION

The present invention is directed to compositions and methods for diagnosis, prevention and treatment of disease states associated with amyloidosis. In accordance with the present invention, compositions and methods are provided that are effective in detecting and treating amyloid deposition, especially amyloid deposition related to neurodegenerative diseases. In a preferred aspect, amyloid deposition is detected and treated by compositions comprising a fusion protein, comprised of a segment comprising an antibody or antibody fragment that binds to an amyloid peptide epitope and a segment capable of crossing the blood-brain barrier, such as one or more transferrin moieties. Preferably, the fusion protein composition has amyloid plaque or tangle dissolving properties and is capable of crossing the blood-brain barrier.

Specifically, the present invention provides for the construction and use of a fusion protein that can detect and treat $\beta$-amyloid deposition. A preferred fusion protein is comprised of an anti-beta-amyloid monoclonal antibody binding region and one or more transferrin moieties. The present invention comprises molecular constructs such as nucleic acid vectors, proteins expressed by such vectors and cells transformed with such vectors and that express the proteins coded for by such vectors.

The present invention also comprises methods and compositions comprising a vaccine that elicits an immune response against amyloid proteins, peptides or fragments, and prevents, stops or hinders amyloid deposition. The vaccine is comprised of an antigen, an amyloid peptide fragment or epitope that is preferably provided in a liposomal bilayer. In an embodiment of the present invention, an antigen is comprised of a modified amyloid peptide, preferably palmitoylated β-amyloid$_{1-16}$ peptide, and methods of administration in a liposomal bilayer.

The invention also provides a method and compositions for preventing or alleviating the symptoms of disease states associated with accumulation or molecular organization of amyloid protein or amyloid plaques in general, including the administration of a pharmaceutically effective amount of a derivaterized amyloid peptide or peptide fragment to a patient.

The present invention includes a pharmaceutical composition in an amount effective to prevent, stop or impede one or more symptoms of a disease state involving abnormal accumulation or molecular organization of amyloid protein, assemblies, fibrils, filaments, tangles, or plaque deposits. The present invention includes an antigen to stimulate production of anti-amyloid monoclonal antibody with the ability to dissolve amyloid plaques. The present invention also provides a method for treating a disease state associated with amyloidosis, including the administration of a pharmaceutically effective amount of the vaccine to a patient.

The present invention also comprises methods for making compositions comprising antisera raised to the epitope of the vaccine compositions of the present invention. These antisera compositions are capable of dissolving amyloid aggregates comprising the epitope or antigen (e.g. β-amyloid). The antisera compositions are effective in the treatment or prevention of the accumulation amyloid protein or the formation of amyloid assemblies, fibrils, filaments, tangles, or plaque deposits and, therefore, disease states associated with amyloidosis.

The invention further comprises methods and compositions for preventing or alleviating the symptoms of disease states associated with accumulation or molecular organization of amyloid protein or amyloid plaques including the administration of a pharmaceutically effective amount of antisera to a patient.

The present invention is particularly useful in the treatment of amyloid-associated diseases, preferably, β-amyloid-associated diseases, including Alzheimer's Disease, Lewy body dementia, Down's Syndrome, hereditary cerebral hemorrhage with amyloidosis (Dutch type), and the Guam Parkinson-Dementia complex or other diseases involving abnormal accumulation or molecular organization of amyloid protein, assemblies, fibrils, filaments, tangles, or plaque deposits.

This and other objects, features, and advantages of the present invention will become apparent after a review of the following detailed description of the disclosed embodiments and the appended claims.

BRIEF DESCRIPTION OF THE FIGURES

FIG. 2A is a map of vector pET24d+.

FIG. 2B is a linear map of vector pET24d+ (SEQ ID NO:3)

FIG. 8 is a $^1$H NMR spectrum of the palmitoylester of N-hydroxysuccinimide. The expected signals are visible.

DETAILED DESRIPTION

Figure 1:
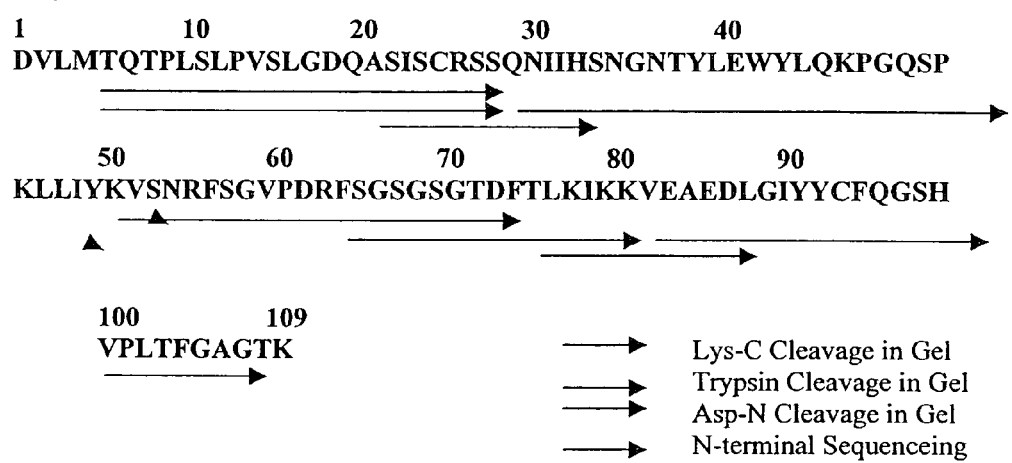
FIG. 1 Sequence of VI chain of 6C6 (SEQ ID NO:4) with sequence sites.

The present invention is directed to compositions and methods for diagnosis, treatment and prevention of diseases associated with amyloid deposition. Preferred compositions of the present invention include compositions comprising fusion proteins capable of affecting amyloid deposits that can cross the blood-brain barrier, and compositions that are effective in raising an immune response to epitopes of amyloid deposits. Preferred methods of the present invention comprise use of the compositions for diagnosis, treatment and prevention of diseases associated with amyloid deposition, and for making and using modified amyloid peptides and molecular constructs of amyloid genes.

An example of one of the diseases associated with amyloid deposition is Alzheimer's Disease, AD. By definition, AD is diagnosed through the examination of brain tissue, usually at autopsy. The currently recommended "minimum microscopic criteria" for AD diagnosis is based on the number of neuritic plaques found in the brain. The amyloid cores of these neuritic plaques are composed of β-amyloid protein, also referred to herein as amyloid-β peptide, that is arranged in a predominately beta-pleated sheet configuration. Brain amyloid plaques are demonstrated by staining brain sections with thioflavin S or Congo red. Congo red-stained amyloid is characterized by a dichroic appearance, exhibiting a yellow-green polarization color. The dichroic binding is the result of the beta-pleated sheet structure of the amyloid proteins.

It is very difficult to diagnose Alzheimer's disease before death, to develop drug therapies, or to treat AD. Screening for apolipoprotein E genotype has been suggested as an aid in the diagnosis of AD. Difficulties arise with this technology, however, because the apolipoprotein E4 allele is only a risk factor for AD, not a disease marker. It is absent in many AD patients and present in many non-demented elderly people. Immunoassay methods have been developed for detecting the presence of neurochemical markers in AD patients and to detect an AD-related amyloid protein in cerebral spinal fluid. These methods for diagnosing AD have not been proven to detect AD in all patients, particularly at early stages of the disease. They are also relatively invasive, requiring a spinal tap. Recently, radiolabeled Aβ peptide has been used to label diffuse, compact and neuritic type plaques in sections of AD brain. These peptides, however, do not normally cross the blood-brain barrier in amounts necessary for imaging.

Congo red may be used for diagnosing amyloidosis in vivo in non-brain parenchymal tissues. But Congo red is probably not suitable for in vivo diagnosis of β-amyloid deposits in brain because only very small amounts, approximately 0.03% of an injected dose of iodinated Congo red, can enter the brain parenchyma. Radioiodinated bisdiazobenzidine compounds related to Congo red, such as Benzo Orange R and Direct Blue 4, have been proposed to be useful in vitro and in vivo to detect the presence and location of amyloid deposits in an organ of a patient. However, like Congo red, all of the compounds contain strongly acidic sulfonic acid groups which severely limit entry of these compounds into the brain.

Attempts have also been made to develop monoclonal antibodies as probes for imaging of amyloid plaques. For instance, antibodies raised against the N-terminal region (1-28) of β-amyloid bind to in vitro-formed β-amyloid assemblies, leading to disaggregation of fibrils and partial restoration of β-amyloid solubility. Some of the monoclonal antibodies raised against soluble β-amyloid (1-28) have also been found to inhibit fibrillar aggregation of β-amyloid peptide in vitro. The success of these attempts, however, has been limited due to the difficulty of getting these large molecules across the blood-brain barrier. Until the present invention, diagnosis, treatment and prevention, of amyloid associated diseases has had little success.

The present invention comprises methods and compositions for diagnosing and treating diseases and processes mediated by the formation of abnormal amyloid deposition, such as amyloid plaques. One aspect of the invention comprises methods of administration of compositions comprising a fusion protein in a dosage sufficient to detect, and preferably dissolve, amyloid plaques. Another aspect comprising methods of making and using compositions comprising vaccine or antisera compositions. The present invention is useful in detecting and treating neurodegenerative diseases, such as Alzheimer's Disease. It is also useful in detecting and treating amyloid plaques in Lewy body dementia, Down's syndrome, hereditary cerebral hemorrhage with amyloidosis (Dutch type) and in the Guam Parkinson-Dementia complex and other amyloid-associated diseases.

An aspect of the invention comprises the construction and administration of fusion proteins comprised of 1) at least one segment of a binding region which binds to an epitope or fragment, preferably an epitope such as one located in β-amyloid and 2) one or more segments comprising portions, fragments or whole proteins that are capable of crossing the blood brain barrier, such as one or more transferrin moieties. The segment comprising the binding region can be any binding partner that is capable of attaching, binding or associating with an amyloid-associated moiety. For example, the variable region of an antibody, including the light or heavy chain or both, can be the binding region that is capable of binding an epitope found on an amyloid protein. In a particular aspect of the invention, the variable region of the light-chain of the 6C6 anti-β-amyloid mAb was sequenced and cloned with human transferrin to produce a molecular construct that expressed fusion proteins: $V_L$-Transferrin and $V_L$-(Transferrin)$_2$. The fusion proteins retained the property of the antibody 6C6 to solubilize β-amyloid fibers and tangles. The addition of the transferrin moieties allows the fusion protein to cross the blood-brain barrier.

The present invention also comprises genes which code for these fusion proteins, expression vectors which contain these genes, microorganisms and cells transformed with these expression vectors as well as a process for the preparation of the genes, proteins, expression vectors and transformed cells and microorganisms.

The present invention further comprises other methods and compositions for preventing or treating diseases and processes associated with amyloidosis. A further aspect of the invention comprises the administration of compositions comprising a vaccine in a dosage sufficient to elicit an immune response against amyloid epitopes, such as proteins or peptides, particularly those found in plaques, tangles or other depositions. It also comprises the administration of compositions comprising antisera raised against amyloid epitopes or immungenic regions in a dosage sufficient to combat amyloidosis. This invention is particularly useful for diagnosing, preventing and treating neurodegenerative diseases associated with amyloid deposition, also referred to as amylodi-associated diseases, such as Alzheimer's, and other conditions associated with localized amyloidosis, such as Adult Onset Diabetes.

The present invention is also directed to methods of inhibiting production of Alzheimer-type amyloidosis in a mammal comprising administering a pharmaceutically effective amount of a modified amyloid peptide capable of eliciting an immune response wherein the immune response prevents, hinders, or decreases the amount of amyloid deposition. The alleviation of symptoms related to amyloidosis followed by administration of derivaterized amyloid peptides, such as those described herein, results from stimulation of appropriate immune responses such that accumulation or formation of the amyloid aggregates is significantly altered, slowed or prevented.

Amyloid-associated conditions or diseases include, but are not limited to, Type 2 diabetes mellitus, amyloid A (reactive), secondary amyloidosis, familial mediterranean fever, familial amyloid nephropathy with urticaria and deafness (Muckle-wells Syndrome), amyloid lambda L-chain or amyloid kappa L-chain (idiopathic, myeloma or macroglobulinemia-associated) A beta 2M (chronic hemodialysis), ATTR (familial amyloid polyneuropathy (Portuguese, Japanese, Swedish), familial amyloid cardiomyopathy (Danish), isolated cardiac amyloid, (systemic senile amyloidosises), AIAPP or amylin insulinoma, atrial naturetic factor (isolated atrial amyloid), procalcitonin (medullary carcinoma of the thyroid), gelsolin (familial amyloidosis (Finnish)), cystatin C (hereditary cerebral hemorrhage with amyloidosis (Icelandic)), AApo-A-I (familial amyloidotic polyneuropathy—Iowa), AApo-A-II (accelerated senescence in mice), fibrinogen-associated amyloid; and Asor or Pr P-27 (scrapie, Creutzfeld Jacob disease, Gertsmann-Straussler-Scheinker syndrome, bovine spongiform encephalitis) or in cases of persons who are homozygous for the apolipoprotein E4 allele.

Fusion Proteins

One aspect of the present invention comprises methods and compositions comprising molecular constructs and the resulting expressed proteins or cells transformed by such constructs. Compositions comprising molecular constructs or the expression of such molecular constructs result in compositions of fusion proteins of the present invention comprising fusion proteins having at least one segment that binds to a portion of amyloid, such as a peptide, protein, tangle or plaque; and at least one segment that is capable of crossing the blood-brain barrier. In particular, it is preferred that the segment that binds to amyloid is a binding region of an antibody or antibody fragment that binds to an epitope of amyloid, preferably an amyloid peptide or proteins. More particularly, it is preferred that the binding of the fusion protein to the epitope cause the dissolution of amyloid deposits, prevent deposition of amyloid or detect the presence of amyloid deposits.

Incorporation of genes or other nucleic acid segments, such as coding regions, into expression vectors can be effected using methods known to the skilled artisan. In this context, reference can be made to the textbooks of Maniatis et al. (*Molecular Cloning*, Cold Spring Harbor Laboratory, 1982) and Sambrook et al. (*Molecular Cloning—A Laboratory Manual*, 2nd. ed., Cold Spring Harbor Laboratory, 1989), the contents of both being herein incorporated by reference.

Methods for the expression of molecular constructs of fusion proteins in accordance with the invention are also known to the skilled artisan, and are described in detail in the aforementioned textbooks. The methods generally comprise the following steps:

a) transformation of a suitable host organism with an expression vector in which a gene or coding region is operatively bonded to an expression control sequence;
b) cultivation of the host organism under suitable growth conditions; and
c) extraction and isolation of the desired fusion protein from the host organism. Host organisms include, but are not limited to, gram-negative and gram-positive bacteria, for example *E. coli* and *B. subtilis* strains, yeast, insect cells, human and other animal cells.

A preferred method for producing compositions comprising fusion proteins using recombinant DNA techniques involves (1) sequencing the binding region segment of the fusion protein, for example, the variable region of a light chain of an antibody, (2) generating a synthetic gene for the expression of the variable region, (3) ligating the synthetic gene into a vector, such as the C-terminally $His_6$-tagged pet24d+ vector or pet36b+ vector bearing a C-terminal cellulose binding domain (CBD), (4) expressing this construct in *E. coli*, (5) fractioning the bacterial lysates, (6) purifying the appropriate fractions using Ni-loaded columns, (7) conducting a Western blot of the purified fraction to reveal the desired protein band; (8) amplifying the cDNA of the variable region of the antibody and the cDNA of human transferrin by PCR techniques, (9) inserting the cDNA of the variable region and the cDNA of human transferrin into a baculovirus vector, such as pBlueBacHIS2 B, (10) cloning the $V_L$-transferrin and $V_L$-(transferrin)$_2$ hybrids, (11) verifying the maintenance of the correct coding sequence by sequencing the inserts, (12) analyzing crude extracts of insect cell cultures to verify that they are positive for $V_L$-transferrin by SDS-PAGE, (13) performing Western blot analysis with an anti-$His_6$ to confirm these results, (14) purifying the constructs, (15) labeling the constructs with $^{111}$In, (15) administering the constructs in an appropriate dosage with a suitable carrier, (16) performing external gamma-camera and radioactivity counting studies of the brain parenchyma and vasculature to quantify the constructs' capacity to cross the blood-brain barrier and to determine the presence of amyloid plaques.

The fusion protein compositions described herein have therapeutic utility, particularly in treatment of amyloid-associated diseases. Methods of treatment comprise administration of an effective amount of a composition comprising a fusion protein. The subject is then monitored for changes in amyloid plaques or cessation of symptoms. The methods of administration comprise one-time administration, sequential administrations or long-term bolus or continuous infusion administrations.

The fusion protein compositions are preferably administered to the mammal in a carrier. Suitable carriers and their formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of a pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the fusion protein, which matrices are in the form of shaped articles, e.g., films, liposomes or microparticles. It will be apparent to those persons skilled in the art that certain carriers may be more preferable depending upon, for instance, the route of administration and concentration of protein being administered.

The fusion protein compositions can be administered to the subject, preferably an animal, mammal or human, by injection (e.g., intravenous, intraperitoneal, subcutaneous, intramuscular), or by other methods such as infusion that ensure its delivery to the bloodstream in an effective form. The compositions may also be administered by intratumoral, peritumoral, intralesional, or perilesional routes, to exert local as well as systemic therapeutic effects. Local or intravenous injection is preferred.

Effective dosages and schedules for administering the fusion protein compositions may be determined empirically, and making such determinations is within the skill in the art. Those skilled in the art will understand that the dosage of protein that must be administered will vary depending on, for example, the subject which will receive the composition, the route of administration, the particular type of fusion protein in the composition and other drugs being administered to the subject. A typical daily dosage of the fusion protein in the compositions of the present invention range from about 1 µg/kg to up to 100 mg/kg of body weight or more per day, depending on the factors mentioned above.

The fusion protein compositions may also be administered to the subject in combination with effective amounts of one or more other therapeutic agents. It may be administered sequentially or concurrently with the one or more other therapeutic agents. The amounts of fusion protein compositions and therapeutic agents depend, for example, on what type of therapeutic agents are used, the condition being treated, and the scheduling and routes of administration. Following administration of such individual compositions or mixtures of compositions to the subject, the animal's physiological condition can be monitored in various ways well known to the skilled practitioner.

Fusion protein compositions may further be used in diagnostic assays for detecting specific antigens or as a nucleic acid probe for, e.g., detecting the presence or expression in specific cells, tissues, or serum, in vitro or in vivo. Various in vitro diagnostic assay techniques known in the art may be used, such as competitive binding assays, direct or indirect sandwich assays and immunoprecipitation assays conducted in either heterogeneous or homogeneous phases. See Zola, Monoclonal Antibodies: A Manual of Technicrues, CRC Press, Inc. (1987) pp. 147–158.

The molecular constructs or expressed proteins used in the present invention can be labeled with a detectable moiety. The detectable moiety preferably is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed.

In a further embodiment of the invention, there are provided articles of manufacture and kits containing compositions comprising fusion proteins that can be used, for instance, for therapeutic methods or other applications described above. The article of manufacture comprises a container with a label. Suitable containers include, for example, plates, slides, bottles, vials, and test tubes. The containers may be formed from a variety of materials such as glass or plastic. The container holds a composition which includes an active agent that is effective for therapeutic or non-therapeutic applications, such as described above. The active agent in the composition can comprise the molecular construct or fusion protein. The label on the container indicates that the composition is used for a specific therapy other application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

Vaccine Methods and Compositions

Additional methods and compositions of the present invention comprise compositions comprising at least one modified peptide, fragment or protein, preferably delivered in liposomal bilayers such as liposomes, that are used in methods to elicit an immune response. Preferably, these immune responses are able to overcome immune tolerance to "self" proteins. It is desirable to elicit such immune responses against amyloid peptides in order to treat or prevent amyloidosis. The products of the immune response are used to effect amyloid deposits, preferably in solubilizing amyloid aggregates. The products of the immune response, including but not limited to, antibodies, anitsera, stimulated cells and cellular factors, and antigens of modified amyloid nature, peptides, fragments or proteins, comprise compositions of the present invention.

A preferred embodiment of the present invention comprises compositions of and methods of using a modified peptide, preferably, $A\beta_{1-16}$, to elicit an immune response. The immune response products or the immune response in vivo are used to dissolve or partially dissolve amyloid deposits. It is desirable to elicit an immune response against β-amyloid 1-16 ($A\beta_{1-16}$). A monoclonal antibody, 6C6, developed against the same epitope, the β-amyloid 1-16 peptide, is capable of solubilizing β-amyloid fibers and tangles in vitro. This particular embodiment relates specifically to Alzheimer's disease and conditions associated with β-amyloid aggregates, but this invention encompasses derivaterized amyloid peptides and their use to elicit immune responses capable of preventing or impeding conditions associated with amyloidosis in general and amyloid-associated diseases.

Preferred compositions comprise peptides that are modified by covalent binding of moieties, such as lipophillic moieties, such moieties are capable of presenting the peptide on the exterior of the delivery agent, such as anchoring the peptide in the lipid wall of a liposome. Preferred methods comprise administration into subjects, such as humans, mammals or other animals, for example, by injection.

Compositions comprising liposomes with modified peptides are used in methods of vaccination and compositions comprising antisera resulting from an immune response to an antigen described herein have therapeutic utility in treatment of amyloid-associated diseases, preferably AD. The compositions are preferably administered to the subject having an amyloid-associated disease. It will be apparent to those persons skilled in the art that carriers may be used, depending upon, for instance, the route of administration and concentration of vaccine or antisera compositions being administered. The vaccine or antisera compositions can be administered to the subject by injection (e.g., intravenous, intraperitoneal, subcutaneous, intramuscular), or by other methods such as infusion to ensure delivery to the bloodstream is in an effective form. Additional routes of administration are included to exert local as well as systemic therapeutic effects.

Effective dosages and administration methods for delivery of the compositions comprising vaccines or antisera may be determined empirically and such determinations are within the skill of an artisan. Those skilled in the art will understand that the dosage required depends on the subject receiving the protein, the route of administration, the particular type of peptide antigen used and other substances being administered, among other considerations.

The vaccine or antisera compositions may also be administered to the subject animal in combination with effective amounts of one or more other therapeutic agents. They may be administered sequentially or concurrently with the one or more other therapeutic agents. The amounts of vaccine or antisera compositions and therapeutic agent depend on the type of therapeutic agents are used, the condition being treated, and the scheduling and routes of administration, among other considerations. Following administration of vaccine or antisera compositions to the subject animal, the animal's physiological condition is monitored in various ways well known to the skilled practitioner.

This invention is further illustrated by the following examples, which are not to be construed in any way as imposing limitations upon the scope thereof. Conversely, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Protein Sequence Analysis of the 6C6 Antibody Light Chain ($V_L$)

The monoclonal antibody 6C6 (Athena Neurosciences, San Francisco, Calif.) recognizes an epitope located in the 1-16 region of β-amyloid and is capable of solubilizing β-amyloid fibers and tangles in vitro. See Tamaoka et al. 1992, Proc. Natl. Acad. Sci, USA, 89, 1345–9.

Light and heavy chains of 6C6 were separated under reducing conditions in an agarose gel. An in-gel Lys-C-digestion with Trypsin was performed on the Kappa light chain using 1 mg Lys-C overnight. Fractions were separated by reverse phase chromatography (HP-C90-1-IPLC 1 mm×12.5 cm, DAD-detector). The mass of collected fractions was determined by mass spectrometry (MALDI-TOF). N-terminal sequencing was performed using a PE-Biosystems-sequencer (Procise ABI 492, Langen, Gemany). Other fragments were obtained by in-gel digests with the endoprotease V-9 cleaving C-terminal of Glu. Peptides were sequenced starting at the N-terminus. The sequence of the $V_L$ chain is given in FIG. 1 and SEQ ID NO:4.

Example 2

Gene Synthesis and Cloning of the V Region of the Light Chain ($V_L$)

The amino acid sequence of the fragment $V_L$ was converted into a nucleotide SEQ ID NO: 1 and inserted into an appropriate vector system. SEQ ID NO:1 includes a methionine residue at position 0 as well as the leucine and glutamine residues at position 109 and 110 as a result of the cloning strategy. The actual DNA sequence of the $V_L$ chain corresponds to SEQ ID NO:4. The $V_L$ gene fragment was synthesized using a PCR-based approach. The sequences of the sense and anti-sense strands were divided approximately into 25 nt oligonucleotides at the 5'-end (external oligo) followed by four 50 mers (internal oligo) in a gapless manner. Internal oligonucleotides were mixed and used as template in a PCR with the two external 5'-oligos as primers, in a 100-fold excess. PCR was performed in 50 µl volume using 1 unit of a proof-reading polymerase (Ultma, Perkin-Elmer) with 2 mM $MgCl_2$, buffers as supplied by the manufacturer and 25 pmol of each external primer. The reaction started 2 minutes after incubation at 99° C. in a Sanyo thermocycler by addition of the polymerase going through 30 cycles at 95° C. for 2 minutes, 66° C. for 2 minutes, and 72° C. for 1 minute. The $V_L$ gene sequence was verified by gel electrophoresis.

Figure 3:
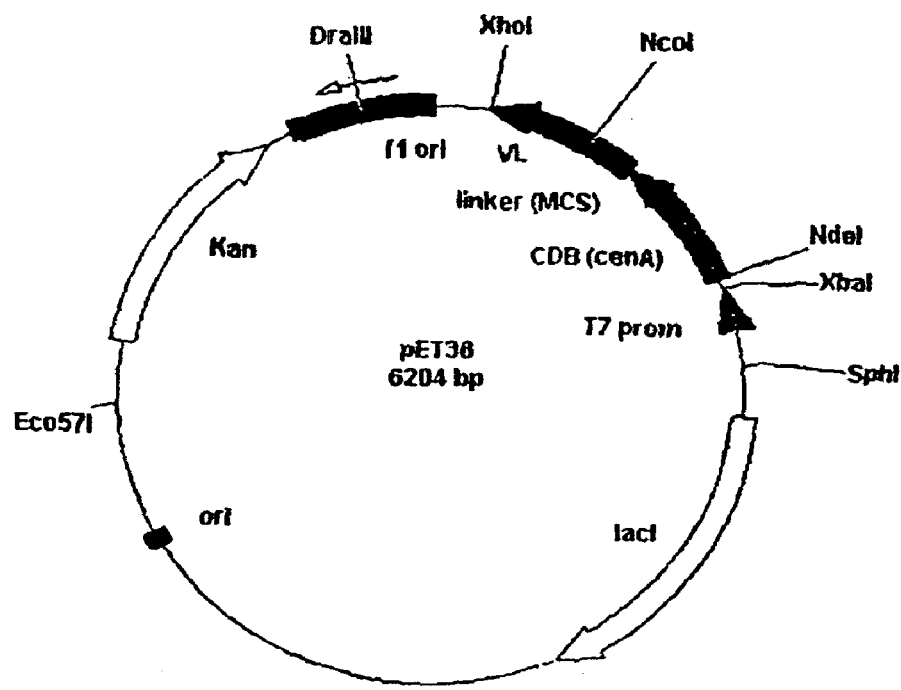
FIG. 3 is a map of vector pET36.

The PCR product was cleaved by NcoI and XhoI. The insert was prepared by agarose gel electrophoresis and ligated into a prepared pET24d+ vector or pET36b+ vector (Novagen), respectively. Initially the plasmid pET24d+ was used to insert the gene fragment ($V_L$) next to a hexa-histidine tag in order to detect and purify the fragment in subsequent experiments. Unfortunately, the anti-His-tag antibodies did not act sufficiently in the detection procedure showing high non-specific binding in Western blot analysis. Therefore, a second expression vector, pET36b+ containing a cellulose-binding domain (CBD) of a prokaryotic cellulase and several short peptide tags was used in order to purify the protein. The CBD included a propeptide acting as signal for the translocation of the CBD to bacterial periplasm. The plasmid pET24d+ containing $V_L$ was named pETVL102; the plasmid pET36b+ with the $V_L$ insert was named pETVL112. The maps of both vectors are given in FIGS. 2 and 3.

Example 3

Expression in E. Coli

E Coli B21 (DE3)pLysS were transformed with the plasmid pETVL102 (pETVL112) and the empty vector pET24d+ (pET36b+) as a control. Overnight cultures were used to inoculate 50 ml of LB-medium containing 50 µg/ml kanamycin and 30 µg/ml chloramphenical. Cultures were grown at 37° C. for 2 hours and agitated at 200 rpm. Expression was induced by the addition of IPTG (final concentration 0.5 mM). 2 ml samples were taken after 2 hours and 4 hours and centrifuged (5 min, 1600×g, 4° C.). The pellets were washed with 1 ml of TrisHCl buffer (25 mlM, pH=7.5) and dissolved in 200 µl of 1×SDS gel-loading buffer (RotiLoad 1, Carl Roth). The samples were sonicated, heated (5 minutes, 95° C.) and analyzed on a 15% SDS-PAGE.

In a subsequent step, expression of the $V_L$-fragment in pETVL112 was repeated on a 2.5 L scale. The total soluble cell fractions were subjected to immobilized nickel affinity chromatography (Ni-1MAC) in a FPLC system. A column of Chelating Sepharose FF (Pharmacia Biotech) charged with Ni2+ ions was equilibrated with Buffer A (25 mM Tris HCl, 0.1 mM NaCl pH=7.5).

A 3 ml sample was loaded, followed by washing with Buffer A containing 20 mM imidazol.Hcl. Elution was accomplished with Buffer A containing 500 mM imidazol-.HCl and the fractions were analyzed in a Western blot.

The rest of the soluble cell extract of E. Coli pETVL112 was treated as described above and fractions around n°58 were pooled. This pool was subjected to a second affinity chromatography using a cellulose matrix. The CBD binds to cellulose in the presence of salt and is eluted either by pure water or by an organic solvent, e.g. ethylene glycol. The pool (20 ml) was forced through two columns (CBinD 900 Cartridges, Novagen). Then, the columns were washed with 10 ml wash buffer (20 mM Tris HCl, 0.8M NaCl, pH=7.5) and 2 ml loading buffer (20 mM Tris HCl, pH=7.5). Each column was eluted with 1 ml 100% ethylene glycol. The flow-through, the washing solution and the eluate, was analyzed in Coomassie blue-stained SDS-PAGE and Western blot.

In sonicated cell fractions only the soluble fraction showed the specific 30 kDa signal. It was concluded that the $V_L$-fragment might be very unstable even if fused to a stable moiety, and that it was not deposited as intracellular inclusion bodies, but processed correctly (unprocessed fusion protein has a calculated mass of about 34 kDa) and translocated to the host's periplasm. For the verification of these results the expression of $V_L$ in pETVL112 was repeated on a larger volume. The results were collected by affinity chromatography on a FPLC system. The absorption was monitored at 290 nm. The imidazol step gradient was used. The specific elution peak was seen at approximately 120 ml total elution volume.

Eluate fractions were analyzed in a Western blot. 7.5 ml of fraction 8, fraction 25, fraction 33, and fraction 58 of the pETVL112 strain and the control (even-numbered lanes) were separated on a 12% SDS-PAGE, transferred to nitrocellulose, incubated with anti-CDB-antiserum, and assayed by protein A-peroxidase conjugate and chemoluminescence. The specific signal was seen in lane 7. Other signals are ambiguous due to a second antiserum that was used to detect the molecular weight marker (M).

The Coomassie blue-stained SDS-PAGE showed no band at the expected position. This suggests a very small amount of the fusion protein is present after this first chromatographic step relative to the total.

The rest of the soluble cell extract of E. Coli pETVL112 was treated similarly and a collection of fractions was forced through columns. Eluate fractions were analyzed by Western blot. The resulting eluate was almost without cross-reacting signals. On the Coomassie blue-stained gel a very faint signal at 30 kDa was visible. See SEQ ID NO:3 and FIGS. 2A and 2B.

Example 4

Construction of $V_L$-Human Transferrin Hybrids

Various $V_L$-transferring hybrids were ligated and cloned into the baculovirus vector pBlueBacHIS2 B (4.9 kb, Invitrogen) for expression in insect cells. The $V_L$ fragment (pETV102) and cDNA for human transferrin (pUC18/hTF, human full length transferrin, 2.3 kb in pUC18 vector, 2.7 kb, obtained from R. T. A. MacGillivray, Department of Biochemistry and Molecular Biology, Vancouver, Canada) were amplified by PCR. The introduction of stop codons and restriction sites at the end of the fragments were done using modified primers.

The following fragments containing either the cDNA of $V_L$ or the cDNA of human transferrin, stop codons, and appropriate restriction sites were successfully amplified:

BamH I-$V_L$-XhoI
Xho IhtF-STOP-Sal I
Xho I-hTF-Bgl II
Bgl II-hTF-STOP-Sal I

Cleavage of the amplified DNA fragments by restriction enzymes allowed the ligation of the purified $V_L$ and transferrin fragments in the following manner:

1. BamH I-$V_L$-Xho I×Xho I-hTF-STOP-Sal 1
2. BamH I-$V_L$-Xho×Xho I-hTF-Bgl II×Bgl II-hTF-STOP-Sal 1

Cleavage 1 yielded a fragment containing $V_L$-TF which was ligated by the restriction site Xho 1 and ended by a stop codon.

In cleavage 2, $V_L$ is connected with transferrin over Xho I followed by a second transferrin connected to the first over the restriction site Bgl II. The fragment ends with a stop codon.

The V-region of the light chain with one transferrin moiety ($V_L$-TF) as well as the V-region with two transferrin molecules ($V_L$-(TF)$_2$) were cloned into the multiple cloning site of the baculovirus vector pBlueBacHIS2 using the restriction sited BamH 1 and Sal I. Insertion of these two selected recombinant clones were verified before sequence analysis.

Starting from pETVL102 the $V_L$ was amplified by PCR using a DNA-polymerase with 3'→5' proofreading-activity. By using $V_L$-specific primers with 5'-terminal extensions, recognition sites for restriction enzymes (5'-end: BamH I, 3'-end: Sal 1) and a STOP-codon following the last amino acid of the $V_L$-fragment were added to the PCR-product.

The purified $V_L$-PCR product and the vector pBlueBacHIS2 B were cleaved with the restriction enzymes BamH I and Sal 1. The restricted vector was dephosphorylated using calf intestine phosphatase (CIP). The restriction products were identified by agarose gel electrophoresis before the $V_L$ fragment was ligated with the CIP-treated pBlueBacHIS2 B vector. The T4 DNA-ligation and CIP treatment were performed as described by the manufacturer (MBI Fermentas). See FIGS. 4(a) and (b).

Example 5

Transformation, Screening and DNA-sequencing of the Subcloned $V_L$ with the Baculovirus Vector pBlueBacHIS2 B Competent *E. Coli* XL-1 Blue MRF cells (Stratagene) were transformed by the ligation product pBlueBacHIS2 B containing the $V_L$-fragment by applying routine procedures (Sambrook et al., 1989. Molecular Cloning: A Laboratory Manual. Cold Spring Harbor Laboratory, New York). After the transformation, six of the resulting clones were tested for the presence of the $V_L$ insert.

The analysis of the single colonies was done by a PCR-based technique using the same $V_L$-specific primers, which were previously used for $V_L$-amplification. Verification of the construct was done by restriction cleavage and sequencing of the inserts.

The BamH I/Sal I-restricted $V_L$-fragment was ligated with BamH I/Sal I, digested, and CIP-treated pBlueBac HIS2 B vector.

After transformation, six of the resulting clones were tested for the presence of the $V_L$-insert. Analysis of single colonies shows that all six clones contained the $V_L$-insert. Clone "$V_L$-1" was selected for further analysis by DNA-sequencing.

Figure 4A:
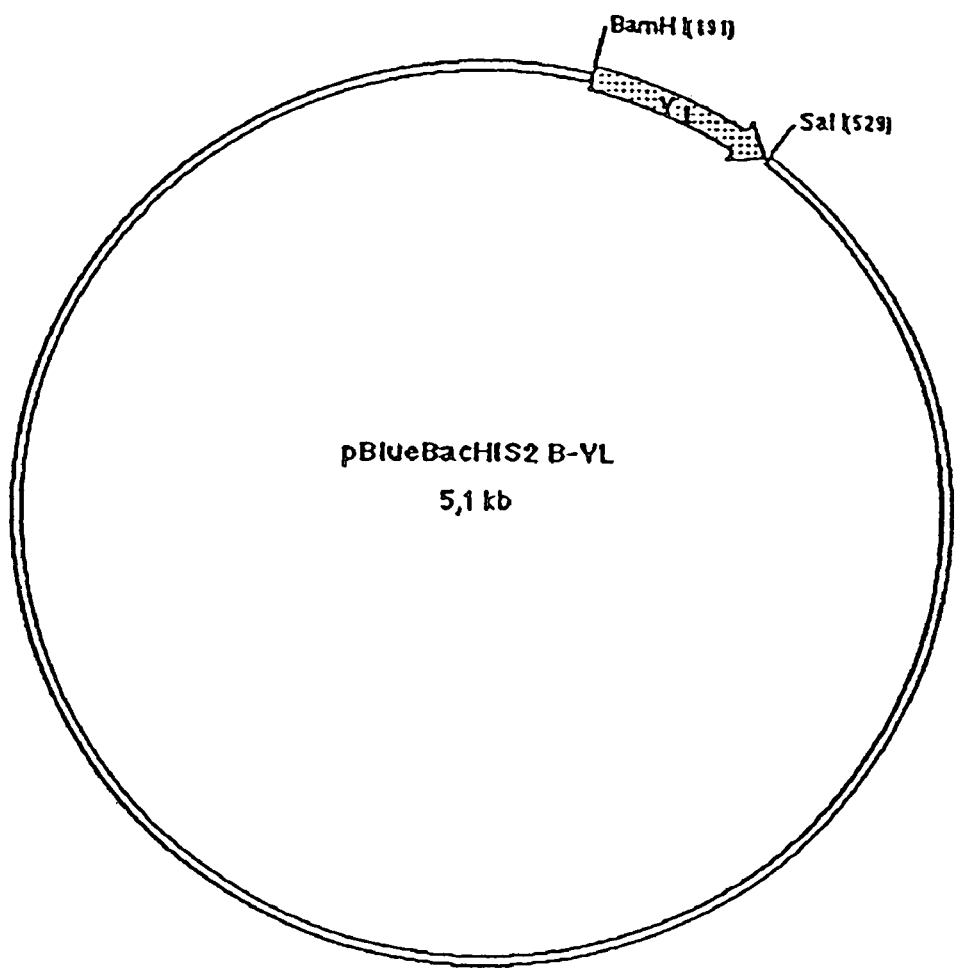
FIG. 4A shows the map of the pBlueBacHIS2 B vector containing the V$_L$ fragment.
Figure 4B:
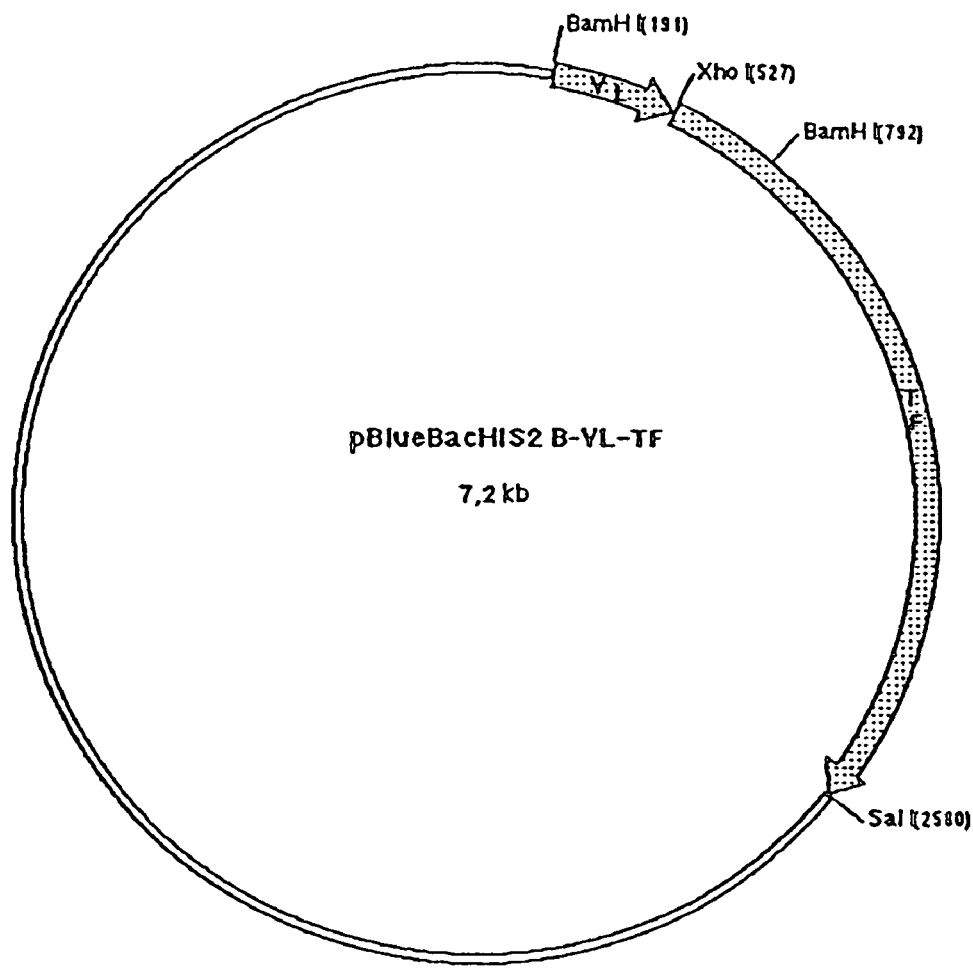
FIG. 4B shows the map of the pBlueBacHIS2 B vector containing the V$_L$-transferrin fragment.

The maintenance of the correct coding sequence was verified by sequencing the inserts pBlueBacHIS B-$V_L$, pBlueBacHIS B-VL-TF and pBlueBacHIS B-$V_L$-TF$_2$. The maps of the pBlueBacHIS2 B containing the $V_L$-fragment and $V_L$-transferrin are shown in FIGS. 4(a) and (b).

Example 6

Generation of the Recombinant Baculovirus and Expression of the Proteins $V_L$, $V_L$-TF and $V_L$-(TF)$_2$ Expression of the fused proteins $V_L$-TF and $V_L$-(TF)$_2$ as well as $V_L$ was performed in *E. coli*. The proteins were analyzed in a Coomassie-stained gel. Three selected plasmids, pBlueBacHIS2 BVL-2, pBlueBacIIIS2 BVL-Tf-4 and pBlueBacIIIS2 B $V_L$L-TF2-5, were verified by DNA sequencing before the in vivo recombination of transfer vector and virus DNA was performed (Ba N-BlueTM Linear DNA, Invitrogen).

Sf9-cells were transfected by the plasmids pBlueBacHIS2 BVL-1, pBlueBacHIS2 BVL-TF-4 and pBlueBacHIS2 B $V_L$-TF2-5 as well as by acceptor-DNA (Bac-N-Blue TM-DNA, Invitrogen). The supernatants were collected after 3 and 5 days and tested in dilutions of 1:10 to 1:10,000 on agarose/X-gal-overlay plates. After 5 days of incubation, viruses were isolated from 8 plaques.

Sf9-cells were infected with these viruses (four samples per plaque) and supernatants were collected 4 days later (named P1-lysates) in order to isolate viral DNA. The DNA was characterized by PCR-technique.

Example 7

Analysis of the Fused Proteins Expressed by the Baculovirus Vector System

For the generation of lysates with a high titer of viruses, $3 \times 10^7$ Sf9-cells were infected with the PI lysates of $V_L$, $V_L$-TF and $V_L$-TF$_2$ with a m.o.i (multiplicity of infection) of approximately 0.1. After 3 days the supernatants were collected and their titers determined by limited dilutions. The proteins were isolated and characterized in a Coomassie-stained 10% PAGE-gel.

The PCR with $V_L$ showed the expected fragments as well as $V_L$-TF in a Coomassie-stained gel. The amplification products of $V_L$-TF$_2$ (light chain with 2 transferrin moieties) seem to have lost one of the transferrin residues showing a length of the product of $V_L$-TF or had lost an even longer fragment. Because of the instability of $V_L$-TF$_2$, the virus DNA of four other clones was analyzed by PCR. Unfortunately, no $V_L$-$TF_2$ with the correct length was detected.

A virus titer of $2\times10^8$ pfu/ml (plaque forming units) for $V_L$-1 (26 ml), $1\times10^8$ pfu/ml for $V_L$-TF4 (26 ml), and $1\times10^8$ for $V_L$-$TF_2$ (14 ml) was obtained from the three selected baculovirus clones $V_L$, $V_L$-TF, and $V_L$-$TF_2$. From the $V_L$- and $V_L$-IF-infected cells, proteins with the expected molecular weights of 15 kD and 80 kD could be extracted. The extract of $V_L$-$TF_2$ showed two proteins with the molecular weight of 80 kD and about 105 kD, both not the relevant protein of $V_L$ fused to two transferrin molecules. Western blot analysis of crude extract of insect cells cultures containing $V_L$ and $V_L$-transferrin performed with an anti-$His_6$ confirmed these results.

Example 8

In Vivo Administration

High grade purification (>95%) of the constructs is performed. A sufficient amount of $V_L$ and $V_L$TF is obtained, and the constructs are labeled with $^{111}$In. External γ-camera and radioactivity counting studies of the brain parenchyma and vasculature allows the quantitation of the constructs' capacity to cross the blood-brain barrier.

Example 9

Preparation of Palmitoylated Lysines for Solid Phase Peptide Synthesis

Figure 5:
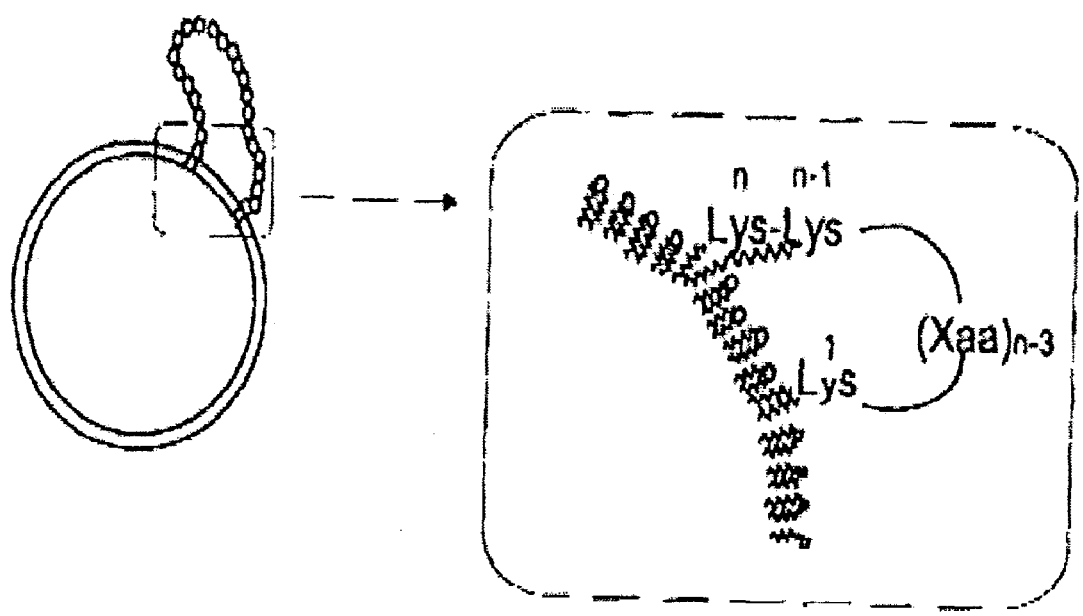
FIG. 5 is the β-amyloid 1-16 (Aβ$_{1-16}$) peptide anchored to the liposomal bilayer by palmitoylated lysines bound to both ends of the Aβ 1-16 peptide.

The following methods were used to produce vaccine compositions. Palmitoylated lysines were appended to both ends of the Aβ 1-16 peptide to anchor the β-amyloid 1-16 ($A\beta_{1-16}$) peptide in the liposome bilayer. See FIG. 5.

Figure 6A:
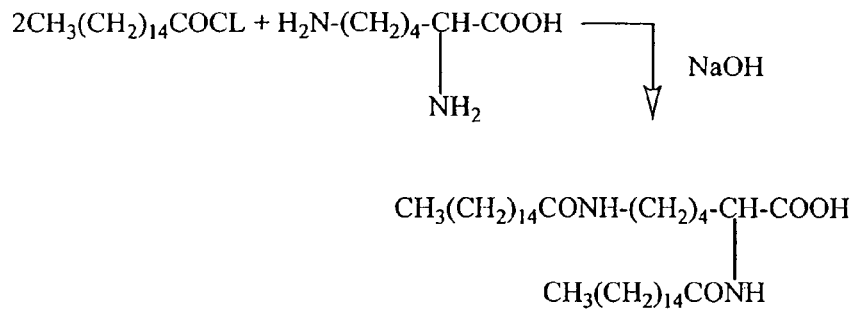
FIG. 6A Synthetic Pathway of dipalmitoyllysine using direct palmitoylation described in Examples 9 and 12.
Figure 6B:
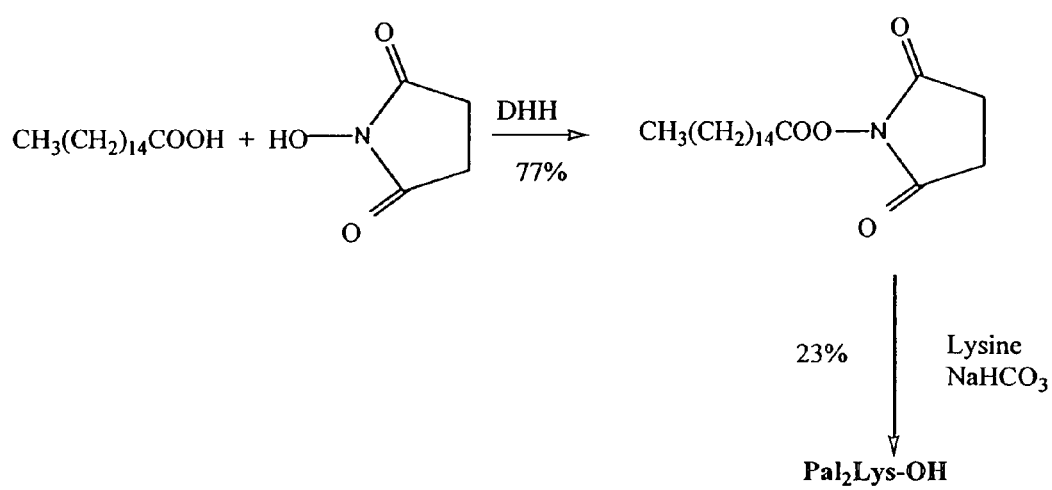
FIG. 6B Synthetic Pathway of dipalmitoyllysine using activated esters described in Examples 9 and 12.
Figure 6C:
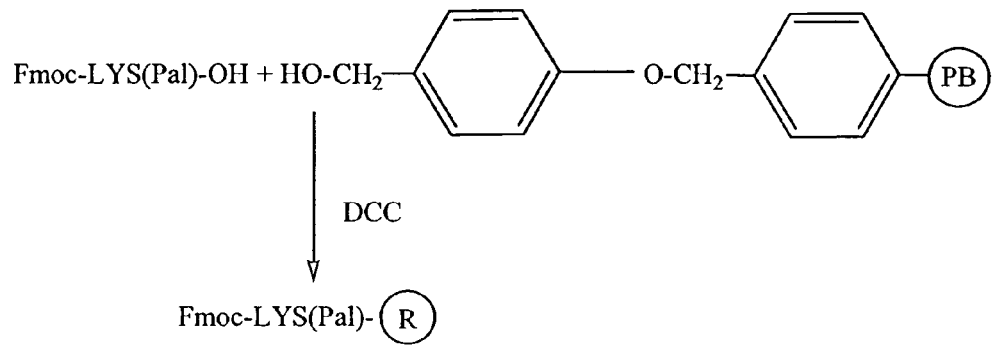
FIG. 6C Solid Phase Synthetic Pathway of the C-Terminus described in Example 9.

Two strategies were adopted and two tetrapalmitoylpeptides were synthesized by means of an Applied Biosystems peptide synthesizer: 1) the N-terminus has two palmitoyl residues, (i.e. α,ε-dipalmitoyllysine) while at the C-terminus two a-palmitoyllysines were inserted sequentially; 2) four a-palmitoyllysines are inserted, two at each end. For the automated solid phase synthesis of the peptide the first amino acid, a-palmitoyllysine, was N-protected and anchored on the 4-alkoxybenzyl alcohol resin by means of an ester linkage. Fluorenylmethoxy-carbonyl (Fmoc) group was preferred as the a-amine protecting group for lysine and its derivatives. Methods for making such building blocks are known. See FIGS. 6 a and b.

Example 10

Anchoring of FmocLys(PAL) on the Alkoxybenzyl Alcohol Resin

FmocLys(Pal)OH (from BACHEM) was reacted with the alkoxybenzyl alcohol resin (from BACHEM) in the presence of dieyclohexylcarbodiimide (DCC, Aldrich) and dimethyl-aminopyridine (DMAP, Aldrich) in dry, freshly distilled methylene chloride according to the procedure optimized by G. Lu et al., *J. Org. Chem.*, 46, 3433 (1981). After stirring for three hours at room temperature, the reaction mixture was filtered and washed thoroughly ten times with dry methylene chloride. To ensure complete reaction, the obtained resin was reacted once more with a fresh portion of FmocLys(Pal)OH, in the presence of DCC and DMAP in dry methylene chloride at room temperature overnight. The next day, after filtration and washing with methylene chloride the resin was dried in vacuum. The FT-IR spectrum of the product shows the expected bands for the ester linkage at 1720 $cm^{-1}$, for the NH group at 3327 $cm^{-1}$ and for the amide carbonyl group 1626 $cm^{-1}$. All these bands are absent in the FT-IR spectrum of the starting alkoxybenzyl alcohol resin. The final quantity was 227 mg with a loading of about 0.5 mmol/g. See FIG. 6(c)

Example 11

Solid Phase Synthesis

To the resin, the second palmitoylated lysine was added by means of FmocLys(Pal)OH after deprotection (removal of the Fmoc group). Then 16 cycles of synthesis were performed for the β-amyloid. For test purposes, a small quantity of this peptide was then cleaved from the resin and investigated by electrospray mass spectrometry (ES-MS). The crude mixture shows the presence of three peptides, the major component being the desired one having peaks at 896.9, 673,0 and 538.0 Da corresponding to the +3, +4 and +5, respectively charged molecular ions. The molecular ion is absent in the spectrum, but can be inferred from this series to be at 2687.86 Da. The other two components correspond to peptides having one or two palmitoylated lysines less (367 Da mass difference) with molecular ions inferred at 2321.43 and 1953.87 Da. This indicates that the coupling of the FmocLys(Pal)OH was incomplete.

α,ε-dipalmitoyllysine was coupled to the rest of the uncleaved resin. Even prolonged coupling times (overnight at room temperature) left unreacted material (ninhydrin test) due to the low solubility in DMF of the dipalmitoylated lysine. After cleavage from the resin, the ES-MS shows that the desired tetrapalmitoylpeptide (M+=3292.43) is present only in about 20%.

In a second run, to avoid the sluggish coupling with α,ε-dipalmitoyllysine, after the 16 cycles which apprehended the B-amyloid residues to the first two palmitoyllysines were completed, two sequential palmitoyllisines were inserted at the end, the coupling being performed twice for each. The ES-MS spectrum after cleavage from the resin (with TFA) shows the desired peaks of the tetrapalmitoylpeptide as the M4+ at 855.4 Da and M5+ at 05.4 corresponding to a molecular ion of 3421.65. This peptide amounts to about 35% or the mixture, the main component being a peptide having two Lys(Pal)-residues less (M+ at 2688.58 Da). A minor component has an extra lysine missing (M+ at 2560.42 Da).

The mixture or peptides was composed of the desired tetrapalmitoylated peptide and peptides lacking palmitoyl residues, thus making the double insertion into liposomes improbable. Therefore, we decided to use the mixtures for liposome preparation.

Example 12

Preparation of α,ε-dipalmitoyllysine

Direct palmitoylation or lysine with palmitoyl chloride in a Schotten-Baumann reaction with aqueous sodium hydroxide, on a 20 g scale led to a material which contained appreciable amounts of palmitic acid and which could not be separated from the desired a,e dipalmitoyllysine. An indirect method had to be adopted following the procedures of H. Kiwada, et al., *Chem. Pharm. Bull.*, 35, 2935–39 (1987); Y. Lapidat, et al., *J. Lipid Res.*, 9, 142–44(1967).

The palmitoylester of N-hydroxysuccinimide was synthesized first from palmitic acid (Fluka), N-hydroxysuccinimide (Aldrich) in the presence of DCC (Aldrich) in ethyl acetate in 77% yield. This activated ester was subsequently reacted with the sodium salt of lysine in aqueous tetrahydrofurane. The crude product obtained after filtration and washing with water still contained some unreacted activated ester as put into evidence by proton NMR and FAB (Fast Atom Bombardment)-mass spectra. Recrystallization from chloroform provided a pure sample of 640 mg. Its FAB-mass spectrum shows the expected peak at 623 Da (MH+) and absence of the peak for the activated ester (354 Da). See FIG. 7 and FIG. 8.

Example 13

Reconstitution of the Palmitoylated Peptides in Liposomes

Liposomes with Lipid A were used as adjuvants in an attempt to break the mouse immune tolerance to Aβ 1-16. They were prepared by mixing dimyristoyl-phosphatidylcholine, dimyristoylphosphatidyl-glycerol, and cholesterol (Avanti Polar Lipids, Alabaster, AI, USA) in the molar ratios 0.9,0.1:0.7. Monophosphoryl lipid A, a strong immunomodulator, (IASL Biologicals, Campbell, Calif., USA) was added at a concentration of 40 mg per mmole of phospholipids. Tosi et al., Biochem. Mophys. Res, Com., 212, 494–500 (1995). The palmitoylated peptides were added at a molar ratio to phospholipids of 1:100 and 1:200. Solvents were evaporated. The resultant film, after hydration with sterile phosphate buffer saline (PBS, pH 7.4) with a final phospholipid concentration 4 mM, was further homogenized by orbital shaking. The liposome suspension was mixed with sterile Alum 15 minutes before injection (9:1 vol:vol, Rehydrogel, HYA, Rebels Inc, Berkley Heights, N.J.).

Example 14

Immunization of Mice

Eight BALB/c mice (Charles River Laboratories, Wilmington, Mass., USA) were immunized by 6 i.p. innoculations at two week intervals with 200 µL of the palmitoylated peptide-liposome/Alum suspension. One group of 3 mice was immunized according to the same protocol with PBS/Alum only. Another group of 3 mice were immunized according to this protocol, with 4 mM phospholipids in PBS and Alum, without palmitoylated Aβ 1-16. Blood was collected from the tail vein 4 days after injection. The collected blood (10–30 µl) was diluted immediately with 10 µl PBS and 5µl heparin. The samples were centrifuged, the serum was removed and tested in an ELISA assay.

A second group of 19 transgenic mice (NORBA, Hoechst Marion Roussel, Bridgewater, N.J.) of different ages, constitutively present β-amyloid plaques on their pancreas. They were immunized using the same protocol described above. Before sacrificing, the immunized NORBA mice received a $5^{th}$ immunization. Blood was collected and assayed for anti-β-amyloid antibodies in an ELISA assay.

Further, 12 B57131/6-mice were immunized as described before. In this group liposomes and palmitoylated β-amyloid (1-16), liposomes; mixed with scrambled β-amyloid (42-1) and liposomes were used for injection. Alum was added as before. As an additional control 3 mice were immunized with liposomes and palmitoylated 13-amyloid (1-16), but without Alum. Blood was collected and tested as described.

Example 15

ELISA (Enzyme-Linked Immunosorbent Assay) Experiments

Microtiter plates were coated with 50 µl of β-amyloid 1–28 solution (1 mg/ml) overnight at 40° C. Blocking of the wells by 200 µl BSA/PBS (0.5% BSA) for two hours at 37° C. followed before washing with 200 µl of PBS/0.005% Tween 20.

Various dilutions of serum (1:100–1:100,000) were incubated for 2 hours at 370 C. The plates were then washed twice with 200 µL of PBS/0.005% Tween 20 before 50 µl of a goat-anti-mouse-antibody (alkaline phosphatase conjugated) in a 1:30,000 dilution was added. After 2 hours at 37° C. the wells were washed as described above. Then, 100 µl of the substrate (PNPP, paranitrophenyl phosphate, 1 tablet in 5 ml distilled water) was added and absorption was measured at 405 nm by an ELISA reader 30–60 min later.

After the third injection with liposomes/palmitoylated β-amyloid (1-16), ELISA assays showed a significant immune response in the vaccinated Balb/c mice. The antibodies were specific to the injected antigen. The $OD_{405}$ of 1:5000-dilutions of the collected sera were 10 to 20 fold higher than those of controls which were dilutions of untreated mice. Thus, this immunization procedure elicited an immune response against Aβ 1-16 in mice. No immune response was detected in the mice having received control immunizations.

The same immunization protocol was used for inoculation of NORBA transgenic mice to study binding to and possibly dissolving of β-amyloid-plaques on their pancreases in vivo. 19 transgenic mice (NORBA, Hoechst Marion Roussel, Bridgewater, N.J.) of different ages, constitutively present β-amyloidplaques on their pancreas, were immunized. Before sacrificing, the immunized NORBA mice received a seventh immunization. Blood was collected and assayed for anti-β-amyloid antibodies in an ELISA assay. In 1:5,000 dilutions of the sera the $OD_{405}$ was 10 fold higher than in controls. The control NORBA mice did not show any anti-Aβ antibodies in their sera. The 3rd group of immunized C57B1/6 mice receiving Aβ 1-16 as well as the scrambled Aβ42-1 and as a control, liposomes without a peptide reached a tenfold higher titer in a 1:10,000-dilution of the sera versus control. See Tables 1 and 2.

TABLE 1

ELISA of sera of Immunized Balb/c and C57B1/6 Mice

| Antigen | Palm β-Amyloid (l-16)/ liposomes, lipid A in C57B1/6 | Scrambled β-Amyloid (42-1)/ liposomes, lipid A | Liposomes, lipid A | Palm β-Amyloid (L-16)/ liposomes, lipid A in Balb/c | Untreated animal Balb/c |
|---|---|---|---|---|---|
| 10000* | 0.16 | 0.06 | 0.011 | — | — |
| 5000 | 0.22 | 0.01 | 0.012 | 0.22 | 0.01 |
| 2500 | 0.46 | 0.024 | 0.060 | 0.30 | 0.04 |
| 1000 | 0.61 | 0.011 | 0.041 | 0.31 | 0.03 |
| 500 | 0.99 | 0.044 | 0.039 | 0.46 | 0.04 |
| 100 | — | — | — | 0.60 | 0.03 |

$OD_{405}$ Dilution: 1-* Secondary antibody: alkaline phosphatase conjugated goat anti mouse antibody. Substrate (PNPP)- p-nitrophenyl phosphate. Assay was performed after the 3. (C57BV6) and after the 4. (Balb/c) booster injection. For each antigen/adjuvants 3 animals were injected.

TABLE 2

Immune response in mice inoculated with palmitoylated β-amyloid (1-16), scrambled β-amyloid (42-1) in combination with liposomes/lipid A and Alum and liposomes without amyloid.

| Antigen | palm.-A$_β$ 1-16 | A$_β$ 42-1 | Phospholipids |
|---|---|---|---|
| number of C57B1/6 mice with a pos. titer in 1:10000 dilution of sera | 2/3 after 5 Injections | 0/3 | 0/3 |
| number of Balb/c mice with a positive titer in 1:5000 dilution of sera | 3/3 after 4 injections | | 0/3 |
| number of transgenic NORBA mice with a pos. titer in 1:5000 dilution of sera | 7/9 (Aventis) after 7 injections | | |

* OD 405 was tenfold of the control (only phospholipids)

Example 16

Pathology Investigation of the Immunized C57B1/6 Mice

The immunized C57B1/6 mice underwent a pathological investigation after the immunization procedure was finished. Sections of kidney, liver, heart, bone marrow, pancreas, spleen and brain were analyzed.

Example 17

Immunohistochemical Investigation of the Pancreas of Vaccinated NORBA Mice

23 NORBA mice of different ages containing β-amyloid-positive and β-amyloid-negative animals were immunized with palmitoylated Aβ (1-16) reconstituted in liposomes, as described (19 mice) or with liposomes only (4 mice). These animals have the β-amyloid plaques on the pancreas instead of brain. The vaccinated mice were sacrificed after the 7$^{th}$ injection and their pancreases were collected and preserved in formalin. The preserved pancreas pieces were soaked in sucrose solution to prepare them for frozen sections. The thin sections obtained were analyzed by Thioflavin T, a fluorescence dye specific for B-amyloid aggregates staining (Vassar and Culling. 1959), to detect B-amyloid on the surface of the pancreas. The sections were analyzed also using a FITC-labeled anti-β-amyloid antibody (Accurate Chemical Co., Westbury. Conn.). The binding of the mouse "autoantibodies" to the β-amyloid plaques was assayed with a rabbit-antimouse IgG, FITC-labeled.

A histological study of Thioflavin T stained sections of pancreases from NORBA transgenic mice, vaccinated with palmitoylated Aβ (1-16) reconstituted in liposomes was performed. The stained pancreatic tissue of a B-amyloid negative animal showed a diffuse, weak, background fluorescence with some bright spots which represented vessels. The acinar cells were completely dark. An 18-month old-animal with fully developed B-amyloid plaques showed intense fluorescence throughout the acinar cell fields. There was also very bright fluorescent areas suggesting larger blood vessels. A 18-month old mouse with fully developed B-amyloid plaques, which was vaccinated and examined 4 months after first inoculation, showed focal (patchy) areas of fluorescence among acinar cells, but predominantly many patches of non-fluorescent acinar cells. The results showed that the vaccination either disintegrated β-amyloid plaques or reversed their deposition.

Quantitative evaluation of the average fluorescence intensity in each section stained with Thioflavin using a luminosity analysis software, indicated that the pancreas sections from 19 months old NORBA vaccinated animals showed less than 25% of the high intensity fluorescence of the same animals, unvaccinated. A sampling of these quantitations is shown in Table 3.

TABLE 3

Percentage of fluorescence intensities in Thioflavin-stained pancreas sections of NORBA mice, vaccinated and unvaccinated.

| Animal | High intensity % | Medium Intensity % | Low intensity % |
|---|---|---|---|
| Control Aβ$^−$ mouse | 0 | 11.65 +/− 1.6 | 88.5 +/− 9.1 |
| Aβ$^+$, 18-month old unvaccinated mouse | 3.271 +/− 0.3 | 34.62 +/− 3.5 | 62.11 +/− 6.1 |
| Aβ$^+$, 18-month old, vaccinated mouse | 0.74 +/− 0.07 | 34.63 +/− 3.5 | 64.63 +/− 6.4 |

Each value is the average of 5 countings. It appears that vaccination reduces dramatically (by more than 70%) the high intensity fluorescence in the Thioflavine-stained pancreas sections of the NORBA transgenic mice with fully developed β-amyloid plaques. The medium and low intensity fluorescence, which is unspecific since it is detected also in the negative controls, remains unchanged upon vaccination, There is no high intensity fluorescence, in the negative controls.

Figure 7A:
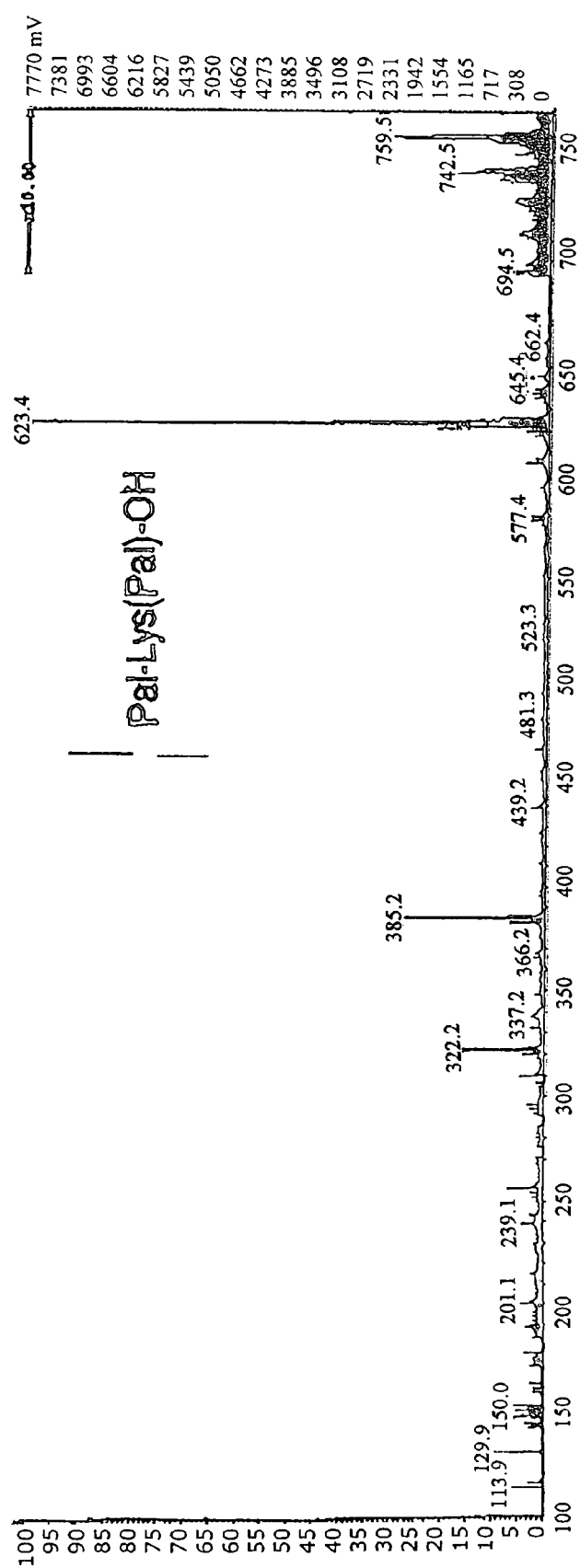
FIGS. 7 A and B are a FAB-mass spectrum of the palmitoylester of N-hydroxysuccinimide. The expected peak at 623 Da (MH+) and absence of the peak for the activated ester (354 Da) are visible.
Figure 7B:
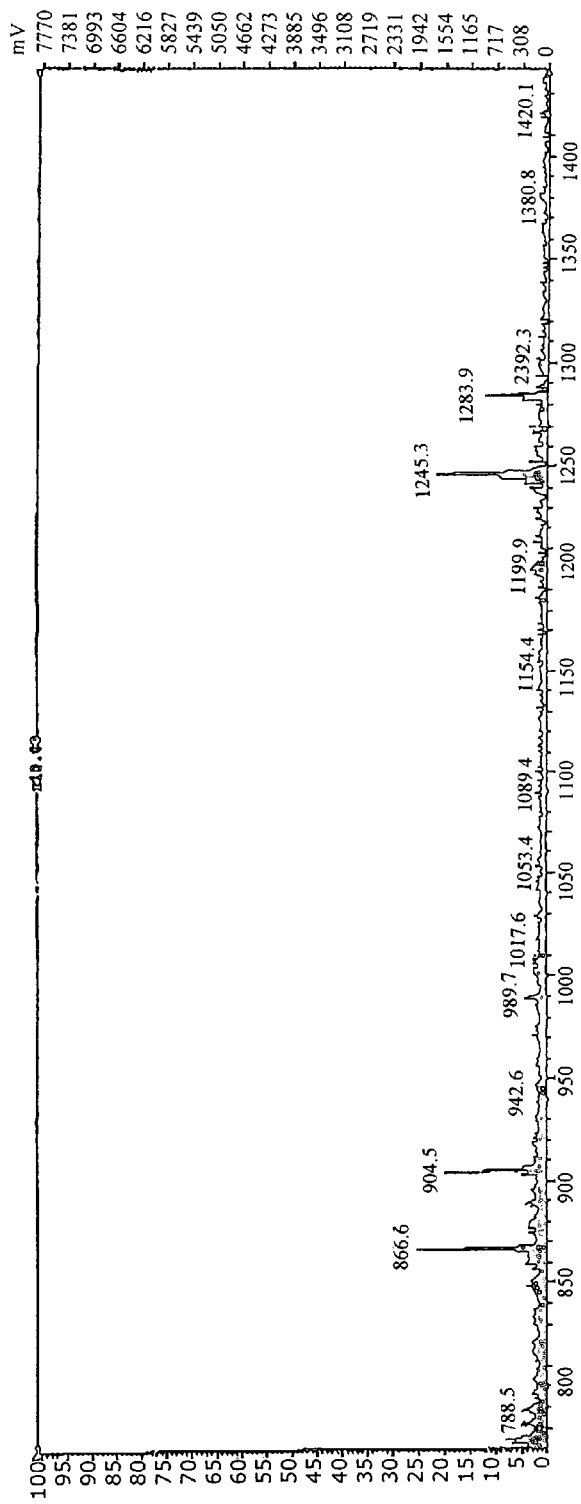
Figure 9:
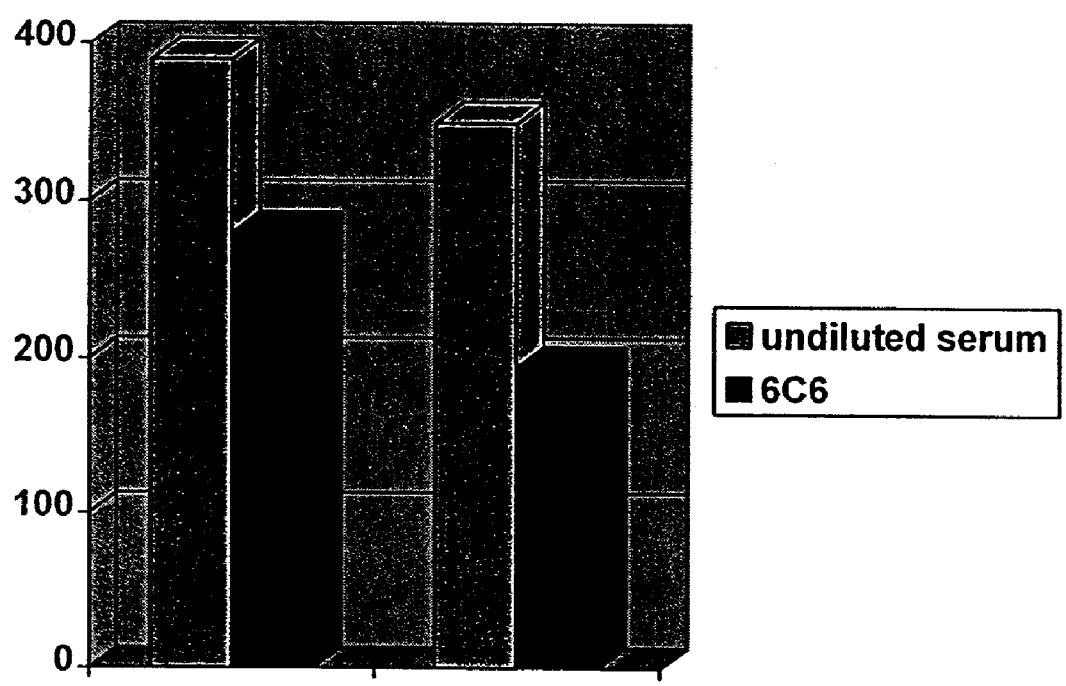
FIG. 9 depicts the disaggregation of β-amyloid fibers by the 6C6=mAB and by sera from mice immunized with palmitoylated Aβ (1-16) reconstituted in liposomes.

In vitro experiments were conducted to investigate the mechanism by which the "autoantibodies" disintegrate the plaques. β-amyloid aggregates using the sequence Aβ (1-28) were made by incubating for 7 days at 37° C. in phosphate buffered saline (PBS) at pH=7.1. This is the sequence used for the immunization of the mice. These deposits were detectable by staining with Thioflavin T ("Th T"). Th T stains amyloid-like deposits and exhibits enhanced fluorescence emission at 482 nm and a new excitation peak at 450 nm when added to a suspension of aggregated β-sheet preparations (Solomon et al.(1997) PNAS 94, 4109–4112). FIG. 7 shows comparatively the disaggregation of β amyloid fibers by the 6C6 mAB and by sera from mice immunized with palmitoylated Aβ (1-16) reconstituted in liposomes.

It appears that both antibodies have solubilizing properties, but the monoclonal antibodies has a significantly stronger effect than the serum from the immunized mice, which contain polyclonal antibodies.

Any patents or other publications mentioned in this specification are indicative of the levels of those skilled in the art to which the invention pertains. One skilled in the art will readily appreciate that the present invention is well adapted to carry out the objects and obtain the ends and advantages mentioned and inherent within. The present examples along with the methods, procedures, treatments, compositions, and specific compounds described herein are presently representative of preferred embodiments, and are not intended as limitations on the scope of the invention. Those skilled in the art will know or will be able to ascertain many equivalents to the specific embodiments of the invention described in the examples above using only routine experimentation. Changes therein and other uses will occur to those skilled in the art which are encompassed within the spirit of the invention as defined by the scope of the claims.

The invention claimed is:

1. A composition comprising modified amyloid beta$_{1-16}$ peptide consisting of amino acids 1–16 of the amyloid beta peptide, wherein the modification consists of one or more covalently bonded lipophilic moieties and wherein the lipophilic moieties are palmitoylated lysines.

2. The composition of claim 1, wherein the modified amyloid beta$_{1-16}$ peptide is anchored in a liposomal bilayer.

3. The composition of claim 1, further comprising a carrier.

4. A composition comprising a modified amyloid beta$_{1-16}$ peptide consisting of amino acids 1–16 of the amyloid beta peptide, wherein the modification consists of one or more covalently bonded lipophilic moieties added to an N terminus of a C terminus of the amyloid beta$_{1-16}$ peptide wherein the one or more covalently bonded lipophilic moieties are one or more palmitoylated lysines.

5. The composition of claim 4 wherein the one or more palmitoylated lysines are added to each of the N-terminus and the C-terminus of the amyloid beta$_{1-16}$ peptide.

6. The composition of claim 4 wherein the one or more palmitoylated lysines are added to the N-terminus of the amyloid beta$_{1-16}$ peptide.

7. The composition of claim 4 wherein the composition is anchored in a liposomal bilayer.

8. The composition of claim 4 further comprising a carrier.

9. The composition of claim 4 wherein the palmitoylated lysines are added to the C-terminus of the modified amyloid beta$_{1-16}$ peptide.

10. A composition comprising a modified amyloid beta$_{1-16}$ peptide consisting of amino acids 1–16 of the amyloid beta peptide anchored to a liposomal bilayer, wherein the modified amyloid beta$_{1-16}$ peptide consists of covalently bonded lipophilic moieties, wherein at least one of the covalently bonded lipophilic moieties is added to a C-terminus of the modified amyloid beta$_{1-16}$ peptide and at least one of the covalently bonded lipophilic moieties is added to an N-terminus of the modified amyloid beta$_{1-16}$ peptide, and wherein the modified amyloid beta$_{1-16}$ peptide is anchored to the liposomal bilayer by at least one of the covalently bonded lipophilic moieties, wherein the covalently bonded lipophilic moieties are palmitoylated lysines.

11. The composition of claim 10 wherein the covalently bonded lipophilic moieties are two palmitoylated lysines added to each of the N-terminus and the C-terminus of the amyloid beta$_{1-16}$ peptide.

12. The composition of claim 10 further comprising a carrier.

* * * * *